(12) United States Patent
Cohen-Solal et al.

(10) Patent No.: US 9,715,575 B2
(45) Date of Patent: Jul. 25, 2017

(54) IMAGE ACQUISITION AND/OR IMAGE RELATED PARAMETER RECOMMENDER (75) Inventors: Eric Cohen-Solal, Ossining, NY (US); Michael Chun-Chieh Lee, Arlington, MA (US); Stefanie Remmele, Hamburg (DE); Sebastian Peter Michael Dries, Hamburg (DE); Julien Senegas, Hamburg (DE); Matthew Joseph Walker, Twinsburg, OH (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/006,694

(22) PCT Filed: Mar. 19, 2012

(86) PCT No.: PCT/IB2012/051298
§ 371 (c)(1),
(2), (4) Date: Sep. 23, 2013

(87) PCT Pub. No.: WO2012/131524
PCT Pub. Date: Oct. 4, 2012

(65) Prior Publication Data
US 2014/0010432 A1 Jan. 9, 2014

Related U.S. Application Data (60) Provisional application No. 61/468,834, filed on Mar. 29, 2011.

(51) Int. Cl.
G06K 9/00 (2006.01)
G06F 19/00 (2011.01)
(52) U.S. Cl.
CPC .......... *G06F 19/321* (2013.01); *G06F 19/325* (2013.01); *G06F 19/345* (2013.01); *G06F 19/3406* (2013.01); *G06F 19/3443* (2013.01)

(58) Field of Classification Search
None
See application file for complete search history.

(56) References Cited

U.S. PATENT DOCUMENTS

| 6,032,678 A | 3/2000 | Rottem |
| 6,574,304 B1 | 6/2003 | Hsieh et al. |

(Continued)

FOREIGN PATENT DOCUMENTS

| JP | 2004357866 A | 12/2004 |
| WO | 2008034182 A1 | 3/2008 |

(Continued)

OTHER PUBLICATIONS

Dale-Jones, R et al. "An advisory system for image enhancement", Proceedings of the lasted International Symposium Artificial Intelligence Application and Neural Networks,—Ainn '09 ACTA Press, US, Jan. 1, 1990 pp. 73-76.

(Continued)

*Primary Examiner* — Soo Park (57) ABSTRACT

A method includes obtaining image data for a patient. The image data corresponds to acquisition data from an imaging acquisition from a set of planned image acquisitions in an examination plan for the patient. The method further includes analyzing the image data with a processor based on an imaging practice guideline and producing electronically formatted data indicative of the analysis. The processor generates a signal indicative of a recommendation of a change to the examination plan based on the data indicative of the analysis.

20 Claims, 3 Drawing Sheets

(56) References Cited

U.S. PATENT DOCUMENTS

| | | | |
|---|---|---|---|
| 6,687,329 B1 | 2/2004 | Hsieh et al. | |
| 7,133,546 B2 | 11/2006 | Dehmeshki | |
| 7,244,230 B2 | 7/2007 | Duggiraia et al. | |
| 7,725,154 B2* | 5/2010 | Beck | A61B 5/055 600/407 |
| 8,000,510 B2* | 8/2011 | Boeing | A61B 6/482 250/370.08 |
| 8,190,450 B2* | 5/2012 | Warner et al. | 705/2 |
| 8,433,111 B2* | 4/2013 | Martin | A61B 5/055 382/128 |
| 8,496,589 B2* | 7/2013 | Watanabe | 600/443 |
| 8,520,920 B2* | 8/2013 | Guehring et al. | 382/128 |
| 8,705,819 B2* | 4/2014 | Carlsen et al. | 382/128 |
| 8,965,080 B2* | 2/2015 | Meetz | A61B 6/032 382/128 |
| 9,317,580 B2* | 4/2016 | Cohen-Solal | G06F 17/30598 |
| 2003/0139944 A1 | 7/2003 | Carlsen et al. | |
| 2007/0239012 A1* | 10/2007 | Boeing et al. | 600/439 |
| 2009/0006131 A1 | 1/2009 | Unger et al. | |
| 2011/0046979 A1 | 2/2011 | Tulipano et al. | |
| 2011/0210734 A1* | 9/2011 | Darrow et al. | 324/309 |
| 2013/0072781 A1* | 3/2013 | Omernick | G06F 19/321 600/410 |
| 2013/0311200 A1* | 11/2013 | Cohen-Solal et al. | 705/2 |

FOREIGN PATENT DOCUMENTS

| | | |
|---|---|---|
| WO | 2010109356 A1 | 9/2010 |
| WO | WO 2010109356 A1 * | 9/2010 |

OTHER PUBLICATIONS

Tomandl, B.F. et al., "Comprehensive imaging of ischemic stroke with multisection CT", Radiographics, the Radiological Society of North America, vol. 23, No. 3, May 1, 2003, pp. 565-592.

* cited by examiner

IMAGE ACQUISITION AND/OR IMAGE RELATED PARAMETER RECOMMENDER

This application is a national stage application under 35 U.S.C. §371 of International Application No. PCT/IB2012/051298 filed on Mar. 19, 2012 and published in the English language on Oct. 4, 2012 as International Publication No. WO/2012/131524, which claims priority to U.S. No. 61/468,834 filed on Mar. 29, 2011, the entire disclosures of which are incorporated herein by reference.

FIELD OF THE INVENTION

The following generally relates to medical informatics and is described with particularly application to a system and/or method that recommends adding, modifying and/or deleting medical image acquisitions and/or image related parameters (e.g., acquisition, reconstruction, visualization, etc.) in connection with a set of planned image acquisitions in an examination plan for a patient.

BACKGROUND OF THE INVENTION

Radiology departments and imaging centers perform imaging acquisitions of patients every day via computed tomography (CT), magnetic resonance imaging (MRI), positron emission tomography (PET), single photon emission computed tomography (SPECT), ultrasound (US), and/or other medical imaging modalities. Generally, an imaging order prescribed by a physician for a patient is received by the department or center. The order will typically contain some level of patient history that is then used by a radiologist to create an examination plan that includes one or more image acquisitions to be performed by one or more imaging modalities. The patient is then imaged by a radiology technologist according to the examination plan.

In some instances, additional findings are observed while the images are being acquired. In some of those cases, a radiologist may then select one or more additional imaging acquisitions to add to the examination plan. For example, in an MRI examination, a T2-weighted fast spin-echo sequence may reveal significant edema of the brain that is suspected to be due to cerebrospinal fluid. A technologist may consult with a radiologist who may then elect to add an additional type of sequence, e.g. a T2-weighted fluid attenuated inversion recovery sequence that would suppress the brightness of the cerebrospinal fluid in the image, which may aid in viewing of other structures.

The decision to include an additional image acquisition is typically made during implementation of the examination plan, for example, while scanning a patient. As such, there generally is a need to make quick decisions about adding an image acquisition. Furthermore, the selection of an additional image acquisition is typically based on the radiologist's expertise and impression of the patient's clinical circumstances, and is taken from a list of possible options for image acquisitions. Unfortunately, this can be a tedious and time consuming task, and the list of possible image acquisitions may be voluminous and include image acquisition that are not relevant to the patient's current health state.

SUMMARY OF THE INVENTION

Aspects of the present application address the above-referenced matters, and others.

According to one aspect, a method includes obtaining image data for a patient. The image data corresponds to acquisition data from an imaging acquisition from a set of planned image acquisitions in an examination plan for the patient. The method further includes analyzing the image data with a processor based on an imaging practice guideline and producing electronically formatted data indicative of the analysis. The processor generates a signal indicative of a recommendation of a change to the examination plan based on the data indicative of the analysis.

According to another aspect, a system includes an interpretation engine that analyzes image data for a patient based on an imaging practice guideline. The image data corresponds to acquisition data from an imaging acquisition from a set of planned image acquisitions in an examination plan for the patient. The system further includes a decision component that generates a recommendation based on the analysis. The recommendation includes a change to the examination plan based on the data indicative of the analysis.

According to another aspect, a method includes obtaining electronically formatted patient information for a patient to be or being scanned via an imaging system. The patient information includes at least a list of planned image acquisitions for the patient from an examination plan of the patient. The method further includes obtaining electronically formatted previously imaged patient information for one or more previously imaged patients. The previously imaged patient information includes at least one or more lists of image acquisitions performed for the previously imaged patients. The method further includes generating a signal indicative of at least one recommended additional image acquisition based on the patient information for the patient to be or being scanned including the list of planned image acquisitions for the patient and the previously imaged patient information including the one or more lists of image acquisitions performed for the previously imaged patients.

According to another aspect, a computing system includes computer readable storage medium encoded with computer readable instructions that identify at least one additional image acquisition, from image acquisitions performed on previously scanned patients, to add to a set of planned image acquisitions of an examination plan of a patient. The computing system also includes one or more processors configured to execute the instructions, wherein the one or more processors, when executing the instructions, determines co-occurrences of 1) image acquisitions in the image acquisitions performed on previously scanned patients and absent from the examination plan with 2) image acquisitions in both the image acquisitions performed on previously scanned patients and the examination plan, wherein the identified at least one additional image acquisition includes image acquisitions in the image acquisitions performed on previously scanned patients and absent from the examination plan having co-occurrences that satisfy a predetermined threshold. The computing system also includes a display that presents the identified at least one additional image acquisitions.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
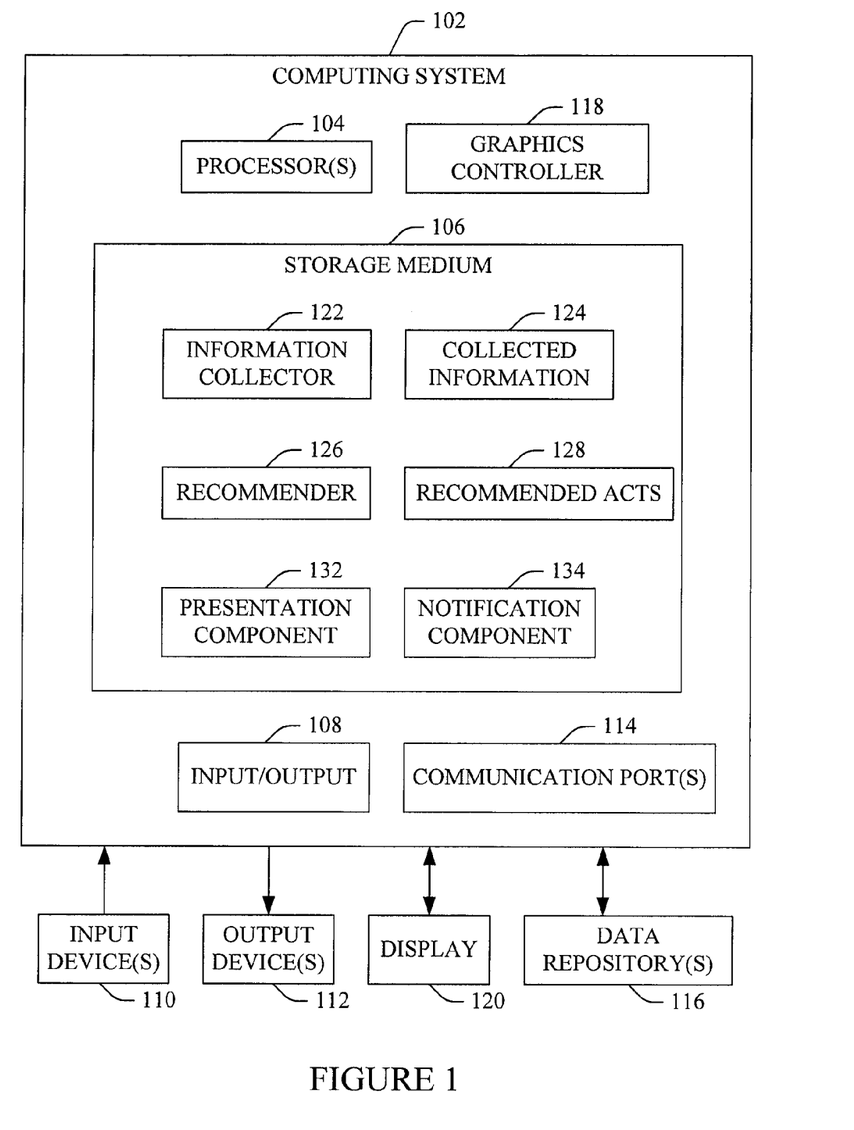
FIG. 1 illustrates an example system that includes a processor(s) and computer readable storage medium with computer readable instructions, which recommends changes to an examination plan for a patient.

FIG. 1 illustrates an example computing system 102 such as a workstation, a computer, a console of an imaging system, or the like.

The computing system 102 includes one or more processors 104 and computer readable storage medium 106 (e.g., physical memory) encoded or embedded with computer readable instructions, which, when executed by the one or more processors 104 cause the system 102 to carry out various functions.

Although the storage medium 106 is showed as a single component, it is to be understood that the storage medium 106 may include a plurality of storage units, including storage local to the computing system 102 and/or storage external from the computing system 102. Additionally or alternatively, the one or more processors 104 execute instructions carried by transitory medium such as a signal or carrier wave.

Input/output 108 is configured for receiving information from one or more input devices 110 (e.g., a keyboard, a mouse, and the like) and/or conveying information to one or more output devices 112 (e.g., a printer, a CD writer, a DVD writer, an optical tape drive, portable flash memory, etc.).

One or more communications ports 114 are configured for communication with an intranet (e.g., within a facility department), an internet (e.g., within and/or amongst facilities), and/or the Internet through various connectors, cables, interfaces, etc. In the illustrated embodiment, the one or more communications ports 114 are configured for communication with various data repositories.

One or more data repositories 116 include information accessible to the system 102, for example, via the one or more communications ports 114. In the context of medical imaging, the one or more data repositories 116 may include one or more of a picture archiving and communication system (PACS), a radiology information system (RIS), a hospital information system (HIS), an electronic medical record (EMR), a database, a server, an imaging system, a computer and/or other data repository. Such data may be stored and/or transferred in standard formats such as Digital Imaging and Communications in Medicine (DICOM), Health Level 7 (HL7), and/or other standard formats, and/or non-standard, proprietary, and/or other format.

A graphics controller 118 processes data for presentation on a monitor such as display 120 or other display in a human readable format.

The illustrated storage medium 106 stores various software applications, software modules, and/or data, which are discussed next.

An information collector 122 collects various electronically formatted information. For example, in one instance, the information collector 122 collects imaging practice guidelines, including, but not limited to, appropriateness criteria and/or other evidence-based guidelines that assist authorized personnel (e.g., physicians and/or other providers) in making an appropriate (e.g., the most appropriate) imaging decision that may take into account factors such as patient safety, patient diagnosis, imaging procedure cost reimbursement, and/or other information. Suitable appropriateness criteria include appropriateness criteria provided by the American College of Radiology (ACR) and/or other guideline clearinghouse.

The information collector 122 additionally or alternatively collects information about a patient to be or being scanned in accordance with one or more image acquisitions in an examination plan of the patient. Such information at least includes a list of planned image acquisitions prescribed for the patient by a physician (e.g. radiologist). By way of non-limiting example, with an MRI scanner, the list may be a list of series (e.g., pulse sequences) to be acquired, which are set up for each patient by the technologist operating the scanner, according to instructions defined by the institution or a particular radiologist. Such information may also include findings, diagnostic conclusion, image data, quantitative metrics, and/or other information corresponding to a performed scan of the examination plan.

The information collector 122 additionally or alternatively collects electronically formatted information about one or more patients already scanned (e.g., other patients and/or the previous scans of the current patient). Such information may at least includes a list of the image acquisitions that were performed for each of the patients, including the image acquisitions that were originally planned in the corresponding examination plans and the image acquisitions, if any, that were added to the original planned image acquisitions.

Optionally, the information collector 122 also collects and stores other information in the order, laboratory information, prior imaging reports, prior non-imaging reports and/or other information of the patient and/or the other patients, diagnostic conclusions used by a clinician to select additional image acquisitions to add to the originally planned image acquisitions of a given examination plan for a previously scanned patient, imaging acquisitions performed in different clinical institutions with comparable imaging equipment, and/or other information.

The information collector 122 can collect the above-noted and/or other information from various data repositories of the one or more data repositories 116 and/or other sources of data. Additionally or alternatively, such information can be provided by a clinician or other authorized personnel. Moreover, such information can be collected before and/or during implementation of an examination plan (e.g., which includes the planned image acquisitions) for a patient. In the illustrated embodiment, the collected information is stored in the storage medium 106 as collected information 124.

A recommender 126 recommends (generates a signal indicative of one or more) one or more, or sets of, image acquisitions and/or imaging related parameters to add, modify and/or delete for a set of planned image acquisitions in an examination plan of a patient. As described in greater detail below, the recommender 126 recommends such information based at least on the information in the collected information 124. In one instance, this includes making such a recommendation based on the image data and appropriateness criteria, a likelihood that the recommendation should be performed, and/or other information. In the illustrated embodiment, the recommendation can be stored in the storage medium 106.

It is to be appreciated that the one or more recommendations may provide information that can improve examination workflow, patient safety, diagnosis, visualization, etc. This may include, for example, allowing for automated and/or quick identification (for the radiologist and/or technologist) of one or more image acquisitions and/or parameters for a given patient. This may be achieved with or independent of the particular radiologist. They imaging system can be provided with this information so that one or more imaging acquisitions and/or related parameters can be added, modified and/or deleted.

Optionally, a list of all or a sub-set of all of the available image acquisitions 130 and/or parameters for one or more facilities is also stored in the storage medium 106 and/or can be obtained by the system 102.

A presentation component 132 variously formats and presents at least the one or more recommended image acquisitions and/or imaging parameters in a user interactive graphical user interface (GUI) of the display 120 and/or other display. In one instance, the presentation component 132 simply presents a list of the such information, and the user can select one or more of the image acquisitions and/or imaging parameters from the presented list, via a mouse click, drag-and-drop, key press or otherwise, to add to the examination plan of the patient. Where multiple sets of additional image acquisitions are recommended based on different parameters, the sets can be individually presented or one or more of the sets can be concurrently presented. In another instance, the recommendation is automatically implemented, with or without authorized personnel confirmation.

In another instance, the list is sorted, for example, based on likelihood, confidence level, and/or other numerical score, which can also be presented. In yet another instance, the one or more recommended additional image acquisitions are presented concurrently with the originally planned image acquisitions. In this instance, the two lists can be visually distinguishable via highlighting (e.g., color, font type, size, etc.), separating into different groups (e.g., two separate lists, etc.), etc. In yet another instance, prior similar patient cases, where image acquisitions were added, are also presented and can be used for comparative purposes. The particular presentation may be based on a pre-determined default or user preference. In still another instance, a list of all available image acquisitions can also presented.

By way of non-limiting example, with an MRI scanner, the display 120 may show the list of most likely pulse sequence candidates from the list of all possibly image acquisitions, as a separate sorted or unsorted list, concurrently with or without the original list of planned image acquisitions. This may allow the clinician to more quickly and accurately locate one or more additional imaging acquisitions (e.g., pulse sequences) to add to the originally planned image acquisitions, relative to a configuration in which a list of all the possible imaging acquisitions are presented alongside the list of currently planned acquisitions.

Where the computing system 102 is part of an imaging system, a selected image acquisition and/or parameter can be directly loaded on the imaging system, automatically or manually in connection with or without user interaction. If not, the selected image acquisition can be conveyed from the computing system 102 to another system such as the imaging system that will be used to scan the patient. Such communication can be via the ports 114, using proprietary and/or standard approaches, such as by transmitting the additional image acquisition via the DICOM modality worklist, etc.

A notification component 134 variously interacts with communication devices such as a cell phone, a pager, a computer, etc. Such interaction may including providing a recommendation to authorized personnel, for example, to apprise personnel of an automated change to a plan and/or imaging parameters, to request confirmation or rejection of a recommendation, etc. Where confirmation is required, the recommendation may be conveyed along with image and/or other information, and recipient of the information can confirm the recommendation via a software application (a cell phone app) resident on the particular communication device, which can be executed by the device.

In the illustrated embodiment, the information collector 122, the collected information 124, the recommender 126, at least part of the recommend acts 128, and the presentation component 132 are shown in the storage medium 106. However, it is to be appreciated that one or more of, or at least part of, 122-132 can be located in other local storage medium and/or external storage medium, including on a single storage medium or distributed across multiple storage mediums.

Figure 2:
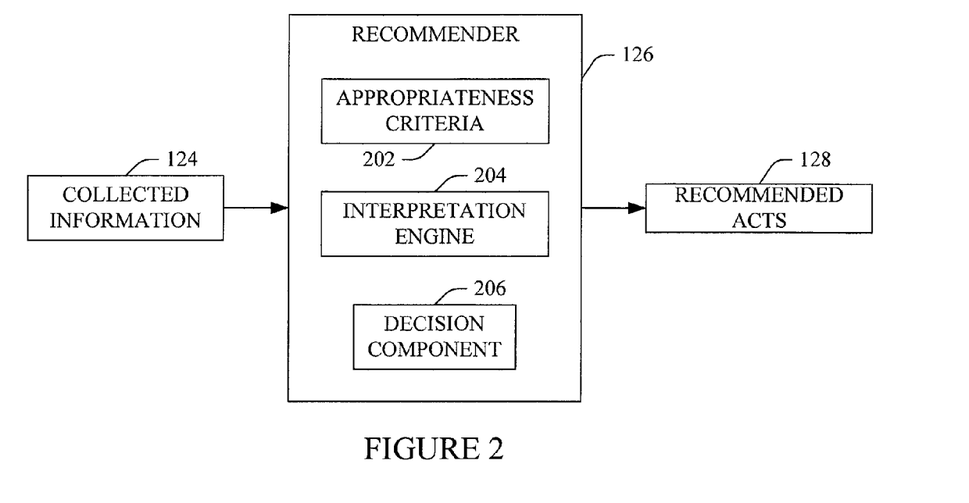
FIG. 2 illustrates an example recommender that bases recommendations on imaging appropriateness criteria.

FIG. 2 illustrates a non-limiting example of the recommender 126.

In this embodiment, the recommender 126 obtains appropriateness criteria 202 and one or more of image data corresponding to a performed scan of the examination plan, findings from the image data, diagnostic conclusions from the image data, various metrics, etc. An interpretation engine 204 analyzes at least a sub-set of the obtained information based on the appropriate criteria 202. A decision component 206 determines, based on the interpretation, to add, modify, and/or delete imaging acquisitions and/or imaging related parameters. The decision is output as the recommendation 128. In this embodiment, the recommender 126 may include a computer aided decision (CAD) system, a computer aided diagnosis (CADx) system, and/or other computer based sub-system.

By way of non-limiting example, the collected information 124 may include a calcium score in a non-contract cardiac scan or the data for the recommender 126 to compute the calcium score. Where the interpretation engine 204 determines that the calcium score satisfies criteria in the appropriateness criteria 202, the decision component 206 can automatically add a contrast-enhanced coronary CTA (or other scan(s) specified by the appropriateness criteria 202) to the set of planned image acquisitions in the examination plan for the patient, if such a scan is not already in the set. In yet another instance, the interpretation engine 204 detects significant coronary stenosis in a contrast-enhanced coronary CTA data from the collected information, and the decision component 206 automatically adds a cardiac CT perfusion (or SPECT/PET perfusion on a CT-NM hybrid system) to the set of planned image acquisitions in the examination plan for the patient.

In another instance, the decision component 206, based on an interpretation of contrast enhanced image data from a cardiac scan by the interpretation engine 204, automatically removes a contrast-enhanced coronary CTA scan from the set of planned image acquisitions in the examination plan for the patient when the decision component 206 determines that such a scan would not provide any further diagnostic information based on the appropriateness criteria 202. In yet another instance, the decision component 206 determines various reconstruction parameters, for example, in order to selectively reconstruct and/or emphasize a particular region of interest in the scan data based on an interpretation by the interpretation engine 204. In still another instance, the decision component 206 determines various visualization parameters to emphasize the particular region of interest.

Figure 3:
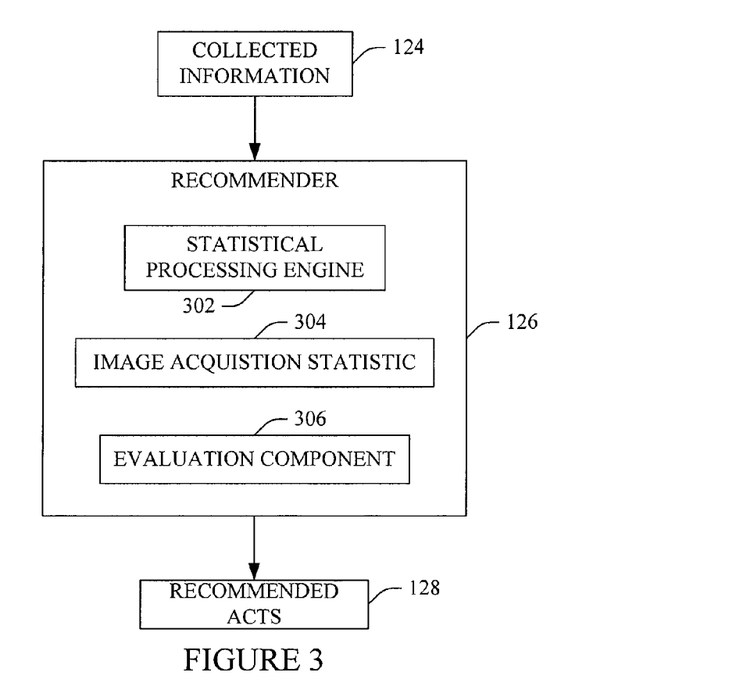
FIG. 3 illustrates an example recommender that identifies the one or more recommended additional image acquisitions to add to the examination plan for the patient based at least on planned and/or added image acquisitions performed on previously imaged patients.

FIG. 3 illustrates a non-limiting example of the recommender 126 in connection with the collected information 124.

A statistical processing engine 302 is configured to compute an image acquisition statistic 304, such as a probability, a likelihood, confidence level, a relevance of each image acquisition, and/or other statistical information. In one non-limiting example, the image acquisition statistic 304 may represent a probability that an image acquisition from the collected information 124 and not in the examination plan should be part of or added to the examination plan based on a co-occurrence of the image acquisition with one or more of the image acquisitions in both the examination plan and the information of the other patients.

For example, in one non-limiting example, the statistical processing engine 302 generate a set of Bayesian probabilities, expressing the probability that an image acquisition 'X' is likely to be part of a patient examination plan given that image acquisitions 'a', 'b', . . . are already planned for that patient: $P(X|a, b, \ldots)$. As an example, the probability may indicate a likelihood that certain MRI pulse sequences are performed in conjunction with the pulse sequences that are already planned. Where clinical data, diagnostic conclusions, and/or other information are available and also used, the probability can be expressed as the probability that an image acquisition 'X' is likely to be performed for a patient given that image acquisitions 'a', 'b', . . . are planned for that patient and that the patient record contains certain clinical concepts. Where clinical data, diagnostic conclusions, and/or other information are represented as 'M', 'N', . . . , then the probability that an image acquisition 'X' is likely to be part of the patient examination can be expressed as $P(X|a, b, \ldots, M, N, \ldots)$.

Additionally or alternatively, the statistical processing engine 302 can produce a series of co-occurrence matrices, where rows and columns represent different imaging acquisitions or combinations of imaging acquisitions. The intersection of a row and column (i.e., an element of the matrix) represents the number of patients for which the two imaging acquisitions or groups of imaging acquisitions were used in each patient in the database of past patients. When normalized, this can be used as estimates to compute the probabilities of different procedures co-occurring with each other. Such matrices can be presented via the display as discussed above in connection with the list of recommended image acquisitions.

An evaluation component 306 evaluates the image acquisition statistics 304. In one instance, if there is any likelihood that an image acquisition should be part of the examination plan, then the image acquisition is included in the recommended acts 128. Where there is no such likelihood, the particular image acquisition is left out of the recommended acts 128. In another instance, the likelihood value has to satisfy a predetermined threshold level for the corresponding image acquisition to be included in the recommended acts 128. Where there is no such likelihood for any image acquisition, no recommendation is made. This may occur in a situation where not enough prior data is available to provide a recommendation, because the probability is too low to suggest a particular acquisition, etc.

Other information such as one or more visualization parameters like contrast, resolution, image quality, etc. can also be utilized by the evaluation component 306 to select which image acquisitions to include in the recommended additional image acquisitions. In one instance, multiple different sets of recommended additional image acquisitions are generated, each based on a different (overlapping or non-overlapping) criteria. For example, a first set may simply be based on co-occurrence, whereas a second set may also based on image quality, and another set can be based on additional or alternative criteria.

Figure 4:
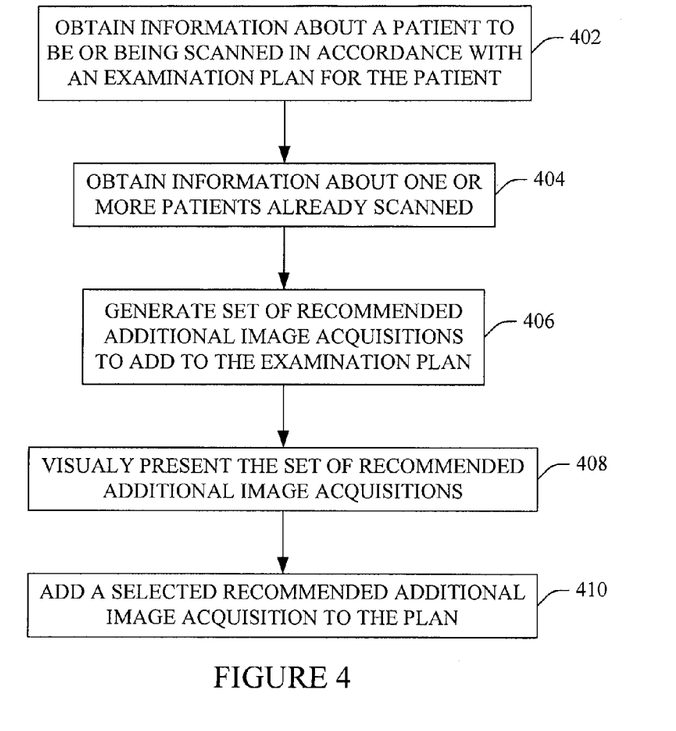
FIG. 4 illustrates an example method for identifying and presenting one or more recommended additional image acquisitions to add to the examination plan for the patient based at least on planned and/or added image acquisitions performed on previously imaged patients.

FIG. 4 illustrates an example method for recommending additional image acquisitions to add to an examination plan for a patient.

It is to be appreciated that the ordering of the acts in the following methods is not limiting. As such, other orderings are contemplated herein. In addition, one or more acts may be omitted and/or one or more additional acts may be included.

At 402, information, in electronic format, about a patient to be or being scanned in accordance with an examination plan for the patient is obtained. As described herein, such information includes, at least, the planned image acquisitions for the patient in the examination plan for the patient. Optionally, other information about the patient, for example, from an imaging order, a laboratory test, imaging and/or non-imaging reports, etc. can be additionally obtained.

At 404, information, in electronic format, about one or more patients already scanned is obtained. This information includes, at least, the planned image acquisitions for the patients and any image acquisition added to the planned image acquisitions for the patients. Optionally, other information about the patient, for example, from an imaging order, a laboratory test, clinical information used to select the additional image acquisitions, etc. can be additionally be obtained.

At 406, a set of recommended additional image acquisitions is generated based on the information about the patient and the information about the one or more previously scanned patients. As described herein, an image acquisition that is not already in the examination plan of the patient is included in the set based on a likelihood that the image acquisition should be part of or added to the examination plan.

Where an image acquisition from the examination plan has already been performed, the resulting one or more images and/or findings therefrom may also be employed to generate the set of recommended additional image acquisitions. Furthermore, other information such as one or more visualization parameters such as contrast, resolution, image quality, etc. may additionally be used to generate the recommended set of additional image acquisitions.

At 408, the set of recommend additional image acquisitions is visually presented to the user. As described herein, the recommended additional image acquisitions can be presented alone or with other information such as the planned image acquisition, non-image acquisition data (e.g., the obtained order, clinical information, etc.) and/or other information. In addition, the recommended additional image acquisitions can be presented in one or more lists, as matrix, and/or otherwise. Further, the clinician can interact with the display to variously sort, select, remove, de-select, etc. one or more displayed image acquisitions.

At 410, one or more of presented recommended additional image acquisitions is added to the examination plan in response to receiving an input indicative of a user selection of one or more of recommended additional image acquisitions. As described herein, selection of a recommended additional image acquisition may result in conveying the additional image acquisition to an imaging system, a PACS system and/or other system, and/or loading the additional image acquisition on the imaging system.

It is to be understood that the information obtained in one or more of the acts 402 or 404 may be obtained and stored for later use by the recommender 126 and/or dynamically obtained when employing the recommender 126. In the illustrated method, the recommender 126 is employed prior to or during implementation of the examination plan.

Figure 5:
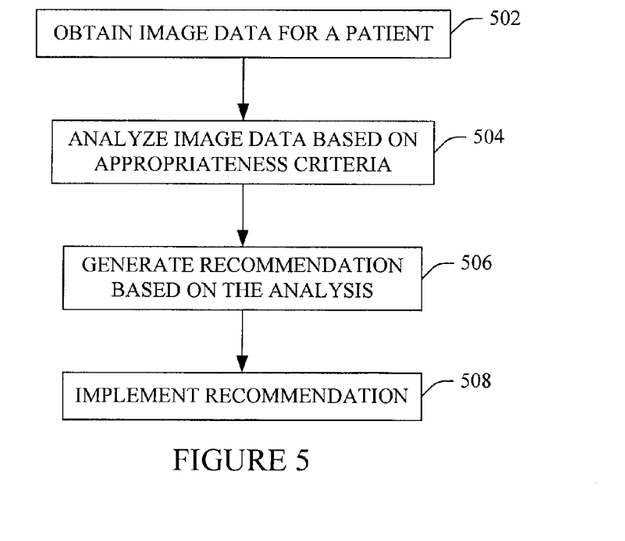
FIG. 5 illustrates an example method for recommending changes to an examination plan for a patient based on imaging appropriateness criteria.

FIG. 5 illustrates an example method in connection with an examination plan for a patient.

It is to be appreciated that the ordering of the acts in the following methods is not limiting. As such, other orderings are contemplated herein. In addition, one or more acts may be omitted and/or one or more additional acts may be included.

At 502, image data for a patient is obtained.

At 504, the image data is analyzed based on appropriateness criteria.

At 506, a recommendation is generated based on the analysis.

At 508, the recommendation is implemented with or without user confirmation.

The above may be implemented by way of computer readable instructions encoded on computer readable medium (e.g., the medium 106), which when executed by a suitable computer processor(s), cause the processor(s) to carry out the described acts.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A method, comprising:
    obtaining, by a processor, image data for a patient, wherein the image data corresponds to acquisition data from an imaging acquisition procedure of a set of planned image acquisition procedures in an examination plan for the patient;
    analyzing, by the processor, the image data based on an imaging practice guideline and producing electronically formatted data indicative of the analysis;
    obtaining, by the processor, electronically formatted previously imaged patient information for one or more previously imaged patients, wherein the previously imaged patient information includes at least one or more sets of performed image acquisition procedures performed for the previously imaged patients and one or more sets of data indicative of prior analyses of the previously imaged patients;
    comparing, by the processor, the planned image acquisition procedures to the sets of performed image acquisition procedures performed for the previously imaged patients to determine a likelihood that a change to the set of planned image acquisition procedures will be required for the patient, based on a comparison of the data indicative of the analysis and the data indicative of prior analyses, and
    providing, by the processor, a recommendation of a change to the set of planned image acquisition procedures based on the likelihood that a change to the planned image acquisition procedures will be required.

2. The method of claim 1, wherein the imaging practice guideline includes appropriateness criteria or other evidence-based guidelines that assist clinical personnel in making an appropriate imaging decision.

3. The method of claim 1, wherein the analyzing includes generating at least one quantitative metric based on the image data, and further comprising:
    comparing the metric with the guideline, and
    basing the recommendation also on a result of the comparing.

4. The method of claim 1, wherein the recommendation includes one or more of adding an image acquisition procedure to the planned image acquisition procedures, modifying at least one of the planned image acquisition procedures, or deleting at least one of the planned image acquisition procedures.

5. The method of claim 1, wherein the recommendation includes changing a reconstruction parameter based on the analyzing of the image data and the acquisition data is reconstructed based on the changed reconstruction parameter.

6. The method of claim 1, wherein the recommendation includes changing a visualization parameter based on the analyzing of the image data and image data is visually presented based on the visualization parameter.

7. The method of claim 1, including automatically implementing the recommendation by the processor.

8. The method of claim 1, including:
    sending a notification to authorized personnel, wherein the notification requests confirmation of the recommendation by the authorized personnel, and
    implementing the recommendation in response to receiving confirmation from the authorized personnel.

9. The method of claim 1, including identifying at least one additional image acquisition procedure that was added to a planned set of image acquisition procedures of an examination plan of the previously imaged patient and is not included in the planned image acquisition procedures of the patient; wherein the recommendation is further based on the at least one additional image acquisition procedure.

10. The method of claim 9, including identifying clinical findings that were used to select the at least one added additional image acquisition procedure; wherein the recommendation is further based on the clinical findings.

11. The method of claim 9, including displaying at least a subset of the set of planned image acquisition procedures concurrently with displaying the at least one identified additional image acquisition procedure; wherein the list of the planned image acquisition procedures and the at least one identified additional image acquisition procedure are displayed so that they are visually distinguishable.

12. The method of claim 1, wherein the recommendation is based on co-occurrences of the planned image acquisition procedures for the patient and the image acquisition procedures of the previously imaged patients and a non-occurrence of at least one of the image acquisition procedures of the previously imaged patients in the planned image acquisition procedures for the patient.

13. The method of claim 12, including determining the likelihood that the at least one of the image acquisition procedures of previously imaged patients should be part of the examination plan, based on the co-occurrence; and wherein the recommendation is based on the likelihood.

14. The method of claim 13, wherein the recommendation includes at least two additional image acquisition procedures, sorted by the respective likelihoods that the additional image acquisition procedures should be part of the examination plan.

15. A system, comprising:
    an interpretation engine that analyzes image data for a patient based on an imaging practice guideline, wherein the image data corresponds to acquisition data from an imaging acquisition procedure from a set of planned image acquisition procedures in an examination plan for the patient;
    a database that stores electronically formatted previously imaged patient information for one or more previously imaged patients, wherein the previously imaged patient information includes analysis data and at least one or more sets of image acquisition procedures performed for the previously imaged patients; and
    a decision component that compares the set of planned image acquisition procedures and a result of the analysis of the image data for the patient to the one or more sets of performed image acquisitions and analysis data of the previously imaged patients and generates a recommendation based on the comparison, wherein the recommendation includes a change to the set of planned image acquisition procedures.

16. The system of claim 15, wherein the imaging practice guideline includes appropriateness criteria or other evidence-based guidelines that assist clinical personnel in making an appropriate imaging decision.

17. The system of claim 15, wherein the interpretation engine generates at least one quantitative metric based on the imaging data, and the decision component bases the recommendation on a comparison of the metric with the guideline.

18. The system of claim 15, wherein the recommendation includes one or more of: adding an image acquisition procedure to the planned image acquisition procedures, modifying at least one of the planned image acquisition procedures, and deleting at least one of the planned image acquisition procedures based on the image acquisition procedures performed for the previously imaged patients.

19. A computing system, comprising:
    computer readable storage medium encoded with computer readable instructions that identify at least one additional image acquisition procedure based on image acquisition procedures performed on previously scanned patients, to be added to a set of planned image acquisition procedures of an examination plan of a patient;
    one or more processors configured to execute the instructions, wherein the one or more processors, when executing the instructions, determines co-occurrences of 1) image acquisition procedures in the image acquisition procedures performed on previously scanned patients and absent from the examination plan with 2) image acquisition procedures in both the image acquisition procedures performed on previously scanned patients and the examination plan, wherein the identified at least one additional image acquisition procedure includes image acquisition procedures in the image acquisition procedures performed on previously scanned patients and absent from the examination plan having co-occurrences that satisfy a predetermined threshold; and
    a display that presents the identified at least one additional image acquisition procedures.

20. The system of claim 19, wherein the display presents at least a subset of the plurality of planned image acquisition procedures concurrently with displaying the at least one identified additional image acquisition procedure; wherein the subset of planned image acquisition procedures and the at least one identified additional image acquisition procedure are displayed so that they are visually distinguishable.

* * * * *